United States Patent
Banko

(10) Patent No.: US 10,758,410 B2
(45) Date of Patent: Sep. 1, 2020

(54) SURGICAL HAND PIECE WITH ULTRASONIC KNIFE

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 121 days.

(21) Appl. No.: 15/783,752

(22) Filed: Oct. 13, 2017

(65) Prior Publication Data

US 2019/0117456 A1    Apr. 25, 2019

(51) Int. Cl.
*A61F 9/007*   (2006.01)
*A61M 3/02*    (2006.01)
*A61M 1/00*    (2006.01)

(52) U.S. Cl.
CPC ....... *A61F 9/00745* (2013.01); *A61M 1/0064* (2013.01); *A61M 3/0283* (2013.01); *A61B 2217/005* (2013.01); *A61B 2217/007* (2013.01); *A61M 2210/0612* (2013.01)

(58) Field of Classification Search
CPC .............. A61M 1/0064; A61M 3/0283; A61F 9/00745; A61B 2217/005; A61B 2217/007
USPC .......................................................... 604/22
See application file for complete search history.

(56) References Cited

U.S. PATENT DOCUMENTS 3,906,954 A * 9/1975 Baehr ................. A61F 9/00763
                                                      606/107
3,976,077 A    8/1976 Kerfoot, Jr.
4,320,761 A    3/1982 Haddad
4,504,264 A    3/1985 Kelman
7,083,589 B2   8/2006 Banko et al.
8,348,967 B2 * 1/2013 Stulen ............ A61B 17/320068
                                                      606/169
8,641,658 B1   2/2014 Banko
2008/0234710 A1  9/2008 Neurohr et al.
2008/0294087 A1 11/2008 Steen et al.
(Continued)

FOREIGN PATENT DOCUMENTS

CN       106175848 A    12/2016
GB       2 293 104 A    3/1996
WO   WO-2017/001379 A2   1/2017

OTHER PUBLICATIONS

International Search Report and Written Opinion in corresponding PCT Application No. PCT/2018/055183, dated Jan. 7, 2019.
(Continued)

*Primary Examiner* — Brandy S Lee
*Assistant Examiner* — Nidah M Hussain
(74) *Attorney, Agent, or Firm* — Leason Ellis LLP

(57) ABSTRACT

A surgical hand piece has a solid knife connected to and supported at its proximal end by a source of ultrasonic energy. A plastic sleeve has the knife located in it. A support is provided between the sleeve and the knife to support the sleeve while minimizing the effect of the vibration of the knife on the sleeve. The space between the knife and the sleeve form a first fluid channel. A plastic fluid tube can be located along the sleeve and can provide a second fluid channel. In order to use the handpiece for cleanup the sleeve can be moved forward to cover the knife and a small aspiration tube can be provided within the sleeve.

14 Claims, 6 Drawing Sheets

(56) References Cited

U.S. PATENT DOCUMENTS

| | | | |
|---|---|---|---|
| 2009/0012520 A1* | 1/2009 | Hixson | A61B 18/1445 606/51 |
| 2013/0144186 A1* | 6/2013 | Furlong | A61B 1/31 600/563 |
| 2014/0329269 A1 | 11/2014 | Adey et al. | |
| 2015/0025451 A1* | 1/2015 | Banko | A61F 9/008 604/35 |

OTHER PUBLICATIONS

International Preliminary Report on Patentability in corresponding PCT Application No. PCT/US2018/055183, dated Apr. 14, 2020.

* cited by examiner

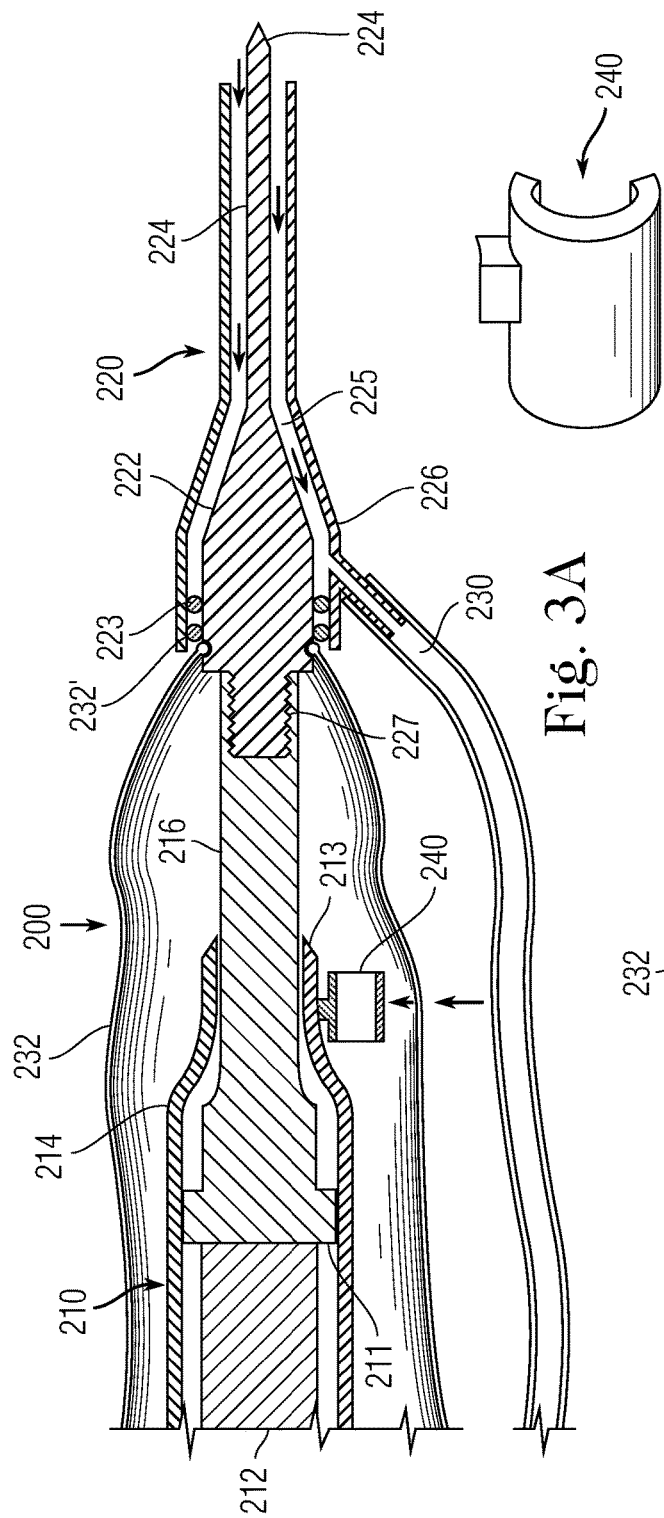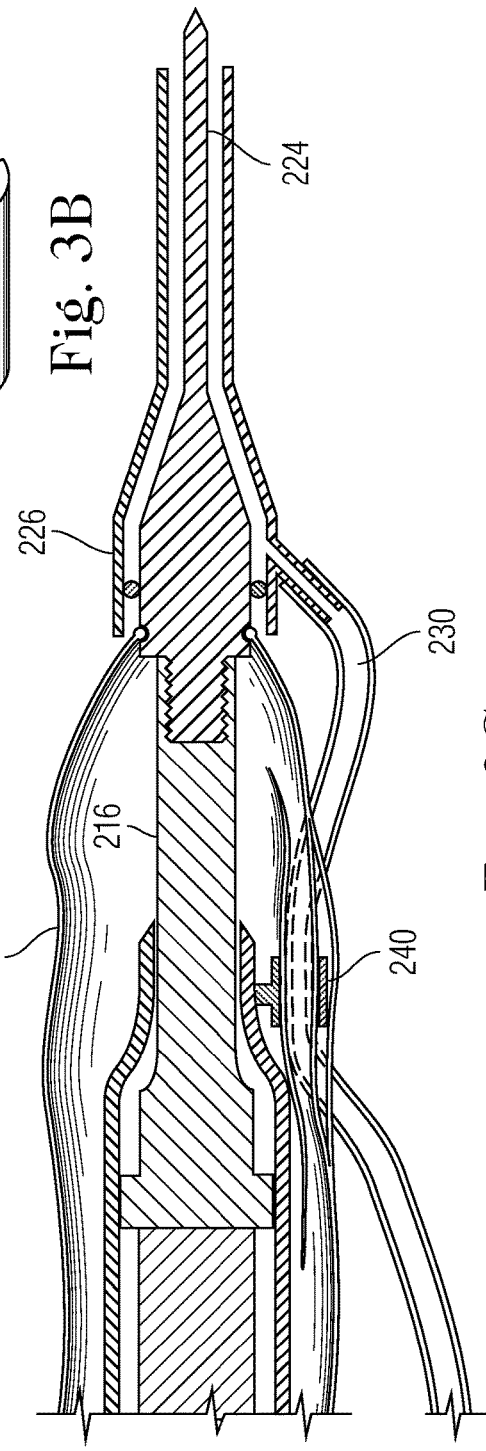
Fig. 3A
Fig. 3B
Fig. 3C

SURGICAL HAND PIECE WITH ULTRASONIC KNIFE

TECHNICAL FIELD

The present invention is generally directed to hand pieces for surgery and particularly for the removal of cataracts from the eye of a patient by phacoemulsification.

BACKGROUND OF THE INVENTION

The use of instruments in ocular surgical applications is well known. One widely used type of instrument is an ultrasonic hand piece that is used in ophthalmic applications, such as in the removal of cataracts from the eye by phacoemulsification.

FIG. 1 depicts one such type of prior art ultrasonic hand piece as shown in U.S. Pat. No. 4,504,264 of Kelman. This hand piece has a housing 10 of, for example, plastic or metal, within which is supported a transducer means 11 for generating mechanical vibrations upon excitation with an alternating-current electrical signal. The transducer 11 is shown as a magnetostrictive transducer with an electrical coil 12 wound about a stack of metal laminations so that longitudinal mechanical vibrations are produced. The transducer can also be of the piezoelectric type. There is a connecting body 16 of, for example, titanium, having a reduced diameter distal end portion, which also can be an attached separate portion. The connecting body forms an acoustic impedance transformer for conveying the longitudinal vibrations of the transducer 11 for application to an operative tool or working tip 14 connected to the distal end of the connecting body 16.

The work tip 14 is connected, such as by a screw thread, to the narrowed distal end of the connecting body 16 so as to be coupled to the transducer 11. As a result, the work tip is longitudinally vibrated by the transducer. The working tip 14 is an elongated, hollow tube of a suitable metal, such as titanium, that is capable of supporting ultrasonic vibrations. It has a distal end of a desired shape to be placed against the tissue to be removed. The work tip 14 has a base portion 15 in threaded engagement with the distal end of the connecting body 16. The tip 14 can be interchanged by use of the screw threads.

The distal end of the tube 14 is shown surrounded by a sleeve 17, which may be made of a material such as silicone, whose proximal end 18 is supported in threaded engagement on a reduced diameter end of the housing 10. If desired, the proximal end of sleeve 17 can be engaged more proximally along the length of the housing 10. The connecting body 16 has two elastomeric O-rings 19, 20 on its outer surface. These provide a fluid-tight seal between the connecting body 16 and the transducer means 11. A plurality of screws 51 are shown disposed around the axis of the housing 10 for preventing longitudinal displacement (other than vibration) or rotational movement of the vibratory structure within the housing and also for radial centering of the vibratory structure within the housing. Other types of conventional mounting arrangements can be used.

The hand piece also illustratively has electrical input terminals 40, 41 for applying a suitable electrical signal to the magnetostrictive transducer 11. Cooling water is shown provided inside the housing 10 from an inlet 42 to an outlet 43 and within a chamber between O-ring 19 and a grommet 50 for circulation around the transducer. This is not always necessary and is not used in most present day hand pieces.

The sleeve 17 around the end of tube 14 forms a first fluid passage 21 between the tip 14 and the sleeve for an infusion/irrigation fluid. An inlet 22 is provided on the housing or sleeve distally of the O-ring 20 for supplying the irrigation fluid to the passage 21 from a fluid supply, e.g., a bag of saline solution (not shown).

A passage 23 is formed through the connecting body 16 that is in communication with a central passage 25 of the work tube 14. An outlet 24 on the housing or sleeve receives a suction (aspiration) force that is applied to the passage 23 in the connecting body and the central passage 25 in the work tip tube 14. A chamber 31 is formed between the spaced O-rings 19, 20 on the body 16 and the housing 10, with which the aspiration force from outlet 24 communicates. Thus the aspiration force is from the source (e.g., a suction pump not shown), into the chamber 31 between the O-rings, through the passage 23 in the connecting body and the passage 25 in the work tip 14. Tissue that is emulsified by impact with the work tip tube 14 is aspirated from the operating site by the aspiration flow force through the tube. In particular, saline solution introduced into the eye through fluid passage 21 and tissue displaced by the vibration force of the tube 14, is drawn into the distal end of passage 25 and passes out of the hand piece through outlet 24. It should be noted that passage 25 is located concentrically within passage 21.

Considering now the operation of the hand piece of FIG. 1. When an electrical signal having a frequency of, for example, 40,000 cycles/second is applied to the coil 12 around the magnetostrictive transducer 11, the transducer 11 vibrates longitudinally at 40,000 cycles per second, thereby vibrating the connecting bodies 13, 16 and the work tip tube 14. Treatment fluid is supplied through inlet 22 and fluid passage 21 to bathe the tissue in the operating site region around the working tip tube 14. Suction force is applied through inlet 24 and passage 23 to the working tip tube 14 passage 25 to withdraw the tissue fragmented by the work tip along with some of the treatment fluid.

Instruments of the type described above are often used in cataract surgery in which the eye lens is removed from the eye capsule and an intra-ocular lens (IOL) is then implanted. In such a procedure before the IOL is implanted it has been found to be desirable to clean up lens substances and lens epithelial cells (LEC's) in the capsular bag of the eye and to remove them. Doing this procedure provides a more stable and long-term fixation for certain types of IOL's in the capsular bag. One manner of accomplishing the cleanup is to use a combination of low force irrigation of the capsular bag interior with a liquid together with the application of low power ultrasonic energy. This dislodges the unwanted cells and substances without damage to the capsular bag. Further, this material can be removed from the capsular bag by the aspiration fluid flow, which also may be reduced in pressure to avoid damage.

In a cleanup procedure it is advantageous if the flow of the irrigation liquid can be made more directional than would be possible using the hand piece with the outer sleeve through which the liquid flows and exits from around the work tip that produces the ultrasonic energy. It is also better if the aspiration force is lower. As a result, typically a different tip from the one illustrated in FIG. 1, which breaks up the tissue, is used for the cleanup. In fact a completely different instrument called an irrigation or infusion/aspiration (I/A) instrument is often used for this purpose. Such an instrument typically has concentric infusion and aspiration lumens, and typically has no ultrasonic vibration capability. The infusion fluid is in an outer concentric lumen so that its flow surrounds the distal part of lumen of the work tip. The aspirated tissue enters a small hole in the distal part and is withdrawn through the central lumen. Thus, when the phacoemulsification has been completed and cleanup is to be started, the surgeon must remove the phacoemulsification tool from the eye. Then the surgeon removes the first or phacoemulsification work tip, replaces it with a different cleanup work tip and then inserts the new work tip or a separate I/A tool is inserted in to the eye. This second insertion into the eye increases the possibilities of infection and trauma. Also, the I/A tool has a disadvantage in that the surgeon would have to keep inserting and withdrawing the ultrasonic work tip and the I/A tool from the eye as the process is completed, because the surgeon cannot be sure that all of the tissue has be broken up until the cleanup process has begun. As a result, this would also subject the patient to the increased possibilities of infection and trauma.

As shown in the present inventor's own U.S. Pat. No. 8,641,658, the surgical instrument may be provided with dual lumens in tubes 132, 134, each of which can alternatively be used for aspiration of emulsified tissue and irrigation of the surgical site. FIG. 2 shows a work tip 130 that can be connected to an ultrasonic energy source 102 of a hand piece by means of a connecting body 204. Two fluid passages 120 and 180 for aspiration or irrigation fluid pass through the connecting body 204. For example the proximal end of passage 120 can be in communication with the irrigation fluid input of the supply line 124 and the proximal end of passage 180 can be in communication with the aspiration fluid of the supply line 164. The distal ends of the two passages 120 and 180 terminate at the distal end of the connecting body 204.

There are threads 182 around the connecting body distal end. A hub 190 is around the proximal ends of the work tip tubes 132 and 134, which are bent so that the proximal ends of their lumens are parallel to the distal ends of the connecting body passages 120 and 180. A collar 194 with internal threads on its open end has its flange end rotatably mounted in a groove 192 in the hub 190. There are mating index pieces, such as mating grooves and ribs or pins (not shown), on the opposing faces of the connecting body 204 distal end and the hub 190 so that the proximal end of the lumen of tube 132 will be aligned with the distal end of connecting body passage 120 and the proximal end of the lumen of tube 134 aligned with the distal end of passage 180.

When the tubes and connecting body are properly aligned the collar 194 is tightened on the connecting body threads 182 and the lumens at the proximal ends of tubes 132 and 134 will be brought into fluid communication with the distal ends of the connecting body passages 120 and 180. O-rings 193 are provided in the connecting body at the distal ends of passages 120 and 180 to make the communications fluid tight.

Both of the tubes 132 and 134 receive the ultrasonic energy from the source 102 (not shown). A valve (not shown) can be used with the hand piece of FIG. 2 to switch the fluid flow from the sources 124 and 164 to the lumens of tubes 132 and 134 of the integrated work tip. Since both tubes 132 and 134 receive ultrasonic energy the emulsification of tissue and its aspiration can take place through either one in addition to each tube being able to supply irrigation liquid through the different types and shapes of openings at the distal ends of the tubes.

The work tip can be used with only an irrigation/aspiration (I/A) function by turning off the source of ultrasonic energy and only supplying the aspiration and irrigation fluids. Thus, the same instrument can be used for the phacoemulsification function while performing irrigation and aspiration as an operation takes place and also only for I/A functions (no or minimal ultrasonic energy is used) useful for cleaning the capsular bag as described above. This eliminates the need for the surgeon changing instruments and also provides the surgeon with a work tip having two tubes with different shape openings available for both aspiration and irrigation.

Only one of the tubes, e.g., 134, can be used as an I/A work tip. In the oval shaped openings 165 along the tube length can be used alone in the eye capsular bag for the substance and cell cleanup procedure described above. The oval shaped openings 165 allow for both good dispersion of the irrigation fluid or a large area for aspiration of cells and substances dislodged by the irrigation liquid.

Since the beginning of phacoemulsification surgery, cataracts have been removed by ultrasonic vibration of a hollow titanium needle or needles. There has never been any other proposal of a way to remove a cataract by ultrasonic vibration, other than by means of a hollow needle. The reason for this is that the end of the needle or tube contacts the tissue directly. Therefore the pieces of tissue are directly in front of the tube end as they are separated and can be easily drawn into the open end of the tube by the aspiration force. However, in order to provide the ultrasonic energy to the tissue, the thin needle must be made of a very strong material. Also the material should be biocompatible. Titanium has been the material of choice.

Titanium, however, is a material that is hard to work with and is expensive. In the early days of phacoemulsification the cost for surgery was high and the expense of the titanium needle was of no great concern. However, as the surgical cost has come down and since there has been increased pressure to reduce medical costs; the cost of the needle has become significant. The expense of titanium and the difficulty of working with it are even more significant with the present inventor's dual lumen work tip as illustrated in U.S. Pat. No. 8,641,658. With this design, not only are there two titanium tubes, but their proximal ends have significant bends that prove to be a manufacturing challenge when titanium is used.

In prior times and currently with typical procedures, after a phacoemulsification procedure, the instruments (including the work tip tube) were sterilized for use with another patient. However, as disclosed for example, in the present inventor's U.S. Patent Application Publication No. 2015/0025451 A1 (FIG. 5), the work tip and its supporting hub can now be discarded after each use along with a sterile sheet or bag. This saves the expense of sterilization of the handpiece including the work tip, and speeds up the operation so that more patients can receive the surgery in a single day, thus reducing the cost to each. The problem is that this disposable work tip creates even more impetus to reduce its cost.

SUMMARY OF THE INVENTION

In accordance with the invention a surgical hand piece is provided with a solid ultrasonic knife or scalpel made of titanium alloy or a material that is less expensive and easier to manufacture than titanium. Further, plastic or other inexpensive tubes can be provided next to the knife blade to provide both aspiration and irrigation. Thus, instead of the single hollow titanium needle providing emulsification along with an infusion sleeve, or dual titanium needles providing emulsification as well as, irrigation and aspiration, these functions are separated according to the present invention. Thus, according to the invention the emulsification function is carried out only by a single metal blade and the other functions can be carried out with less strong and less expensive tubes laid next to the metal blade. Further, the operation of the aspiration and irrigation tubes can be reversed a needed for phacoemulsification and cleanup.

In an illustrative embodiment the surgical hand piece has a solid blade connected to a source of ultrasonic energy and a sleeve in which the blade is located. There is a support for holding the blade within the sleeve. Because the blade is vibrated at ultrasonic frequency, some vibration can be transmitted to the sleeve. However, the support of the blade in the sleeve is designed to dampen the transfer of vibration of the blade into the sleeve.

Note that from an engineering point of view you do not want to transmit any vibration to the sleeve that surrounds the phacoemulsification blade. All current handpieces have irrigation sleeves attached to the non-vibrating housing of the handpiece. However, if the sleeve is attached to the housing, then you need to have fluid going through the handpiece and you need to autoclave the handpiece. In an embodiment of the present invention the solid vibrating blade (knife) is located within the sleeve so as to form an aspiration channel. Essentially the sleeve surrounds the vibrating blade. Also, efforts are made to isolate the sleeve from the vibrating blade, e.g., with O-rings between the blade and sleeve, where the O-rings are made of Teflon. However, the significant benefit of having some minor vibration transmitted to the sleeve is that the hand piece has no fluid in it and does not need to be autoclaved if it is surrounded by a sterile sheet that is attached to the sterile disposable work tip.

Since the blade is centered in the aspiration tube, the open end of the aspiration tube is ideally located to collect the tissue. Irrigation fluid can be supplied to the surgical site through another tube located along the periphery of the aspiration tube.

The work piece of the present invention can be used not only in cataract surgery but in general surgery or neurological surgery as well.

The principles of the invention have numerous advantages. For example, the invention allows for a less expensive and easier to manufacture work piece. In addition, the design of the present invention allows the work piece to be used both for phacoemulsification and clean up without having to remove the work piece from the surgical site, such as the eye, and to replace it with an I/A clean up tool. Further, according to the present invention, clean up can be commenced without the surgeon having to divert his attention from the eye of the patient.

BRIEF DESCRIPTION OF THE DRAWINGS

The foregoing and other objects and advantages of the present invention will become more apparent when considered in connection with the following detailed description and appended drawings in which like designations denote like elements in the various views, and wherein:

FIG. 3A is a cross-sectional view of a surgical hand piece according to an exemplary embodiment of the present invention, FIG. 3B is an enlarged view of a tube holder for use with the hand piece of FIG. 3A and FIG. 3C shows the embodiment of FIG. 3A with an aspiration tube in the tube holder;

DETAILED DESCRIPTION OF THE INVENTION

Figure 1:
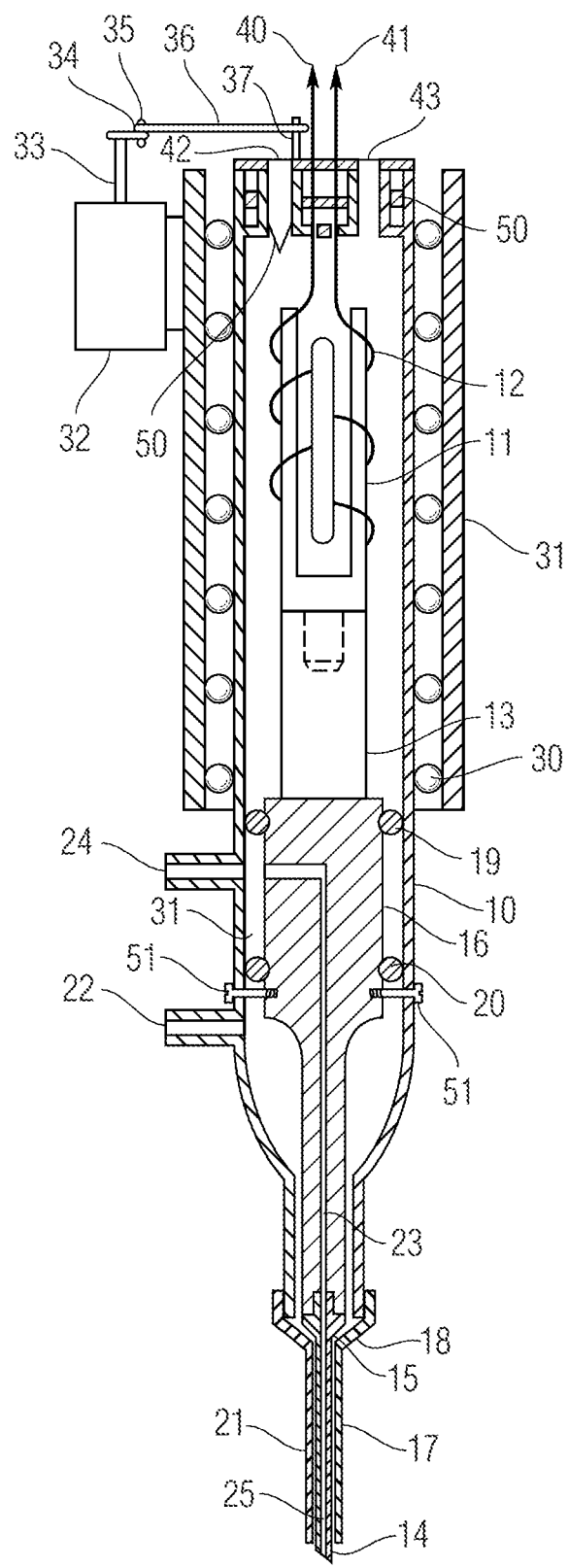
FIG. 1 is a view in partial cross-section of a prior art type of surgical hand piece.

FIG. 3A shows an embodiment of a handpiece 200 according to an illustrative embodiment of the present invention. This hand piece has an ultrasonic vibration part 210 connected to a disposable work piece 220. The vibration part has a housing 214. A transducer 212 is provided in part 210 for generating ultrasonic linear mechanical vibrations upon excitation with an alternating-current electrical signal. The transducer is supported within the housing 214 by flanges 211. A metal connecting body 216 having a reduced diameter distal end portion is attached to the transducer 212. The connecting body forms an acoustic impedance transformer for conveying the longitudinal vibrations of the transducer 212 for application to the operative working tip 220 connected to the distal end of the connecting body 216. Further, the housing has a part 213 that engages the connecting body 216 at a null point in its vibration to provide further support.

The work tip 220 has a hub 222. In an illustrative embodiment a proximal end of the hub 222 has threads 227 that connect to threads in the distal end of the connecting body 216. The distal end of the hub narrows down to form a solid knife or scalpel 224. The working tip also includes a plastic outer sleeve 226 that surrounds the hub and knife. Its proximal end is larger to accommodate the hub. This larger end is reduced in size toward its distal end so as to be formed as the knife. As a result, a relatively uniform channel 225 is created between the inner surface of the outer sleeve 226 and the combination hub and knife. The channel 225 extends from the distal end of the work piece 220 just shy of the end of the knife to a location in the larger part of the outer sleeve 226 at the location of a tube 230. In one embodiment the tube 230 can be used to withdraw aspiration fluid and tissue from the surgical site at the location of the end of the knife. As an alternative, it can be used to provide irrigation fluid to the same site.

As a result of this structure, the hub 222 and knife 224 of work tip 220 are longitudinally vibrated by the transducer 212. The sleeve 226 may be made of a plastic such as polysulfone. The sleeve is supported with respect to the hub and knife by means of O-rings 223, 223' at its proximal end. These O-rings not only support the sleeve 226, they also reduce the vibration applied to the sleeve from the vibrating hub and knife. Further, these O-rings block fluid in channel 225 from leaking out of the work tip.

A sterile sheath or bag 232 is attached to the proximal end of the hub 222 distally of its attachment to connecting body 216. During operation this bag keeps the sterile surgical site and the work tip 220 from contacting the vibration generating part of the hand piece 210. If that part 210 of the hand piece had not been previously sterilized, the bag eliminates the need to sterilize it for an operation on a new patient. Notice that with this design none of the aspiration fluid enters the part 210 of the handpiece inside of the bag. Instead, the work tip 220 is removed by unthreading the hub 222 from connecting body 216, and the bag and work piece are discarded prior to an operation on another patient. No sterilization is needed on the part 210. Thus bag 232, hub 222, knife 224 and sleeve 226 become elements of a disposable single use product. Reducing the cost of this product is a goal of the present invention.

One of the important features of the present invention is that the knife or scalpel 224 is made of solid material and has a rectangular structure that tapers down to a cutting edge at its distal end, as opposed to the elongated, hollow titanium alloy tube of the prior art. See for example FIGS. 5A and 5B. Such a solid blade may have been used in other surgical tools, but it has not been used previously in the removal of cataracts by phacoemulsification. Since the knife has a diameter about the size of the hollow tubes used in the prior art, it is much stronger than those tubes if made of the same material, i.e., a titanium alloy. As a result, the rectangular shape of the knife can be made thinner than the prior art tubes. As an alternative the blade can be made of a weaker material, e.g., surgical stainless steel (type 316L), than the titanium alloy of the prior tubes. Making the blade thinner may not be a good choice because it may lead to bending.

Titanium alloy (Grade 2) is stronger and lighter in weight than surgical stainless steel (type 316L). However, Titanium is about three times the cost. See the article, Young et al, "Titanium is not too Expensive," c.ymcdn.com/sites/www.titanium.org/resource/resmgr/2010.../YoungChuck_2012.pdf. Further, many of titanium's material and component design characteristics make it expensive to machine. A considerable amount of stock must be removed from primary forms such as forgings, plates, bars, etc. In some instance, as much as 50 to 90% of the primary form's weight ends up as chips. See the article "Machining Titanium and Its Alloys," jobshop.com/techinfo/papers/machiningtitanium.shtml. Another choice is to make the knife of a hard ceramic material. By making the solid blade 224 of a less expensive and more easily machined material, the overall cost of the disposable product is reduced.

A tube holder 240, which is shown enlarged in FIG. 3B, is attached to the housing near point 213 and within the sterile bag 232 as shown in FIG. 3A. The aspiration tube 230 can be pushed against the bag 232 until it clips on to the tube holder 240 as shown in FIG. 3C. In this way the tube 230 is secured, but still remains within the sterile environment on the distal side of the bag 232.

Figure 4:
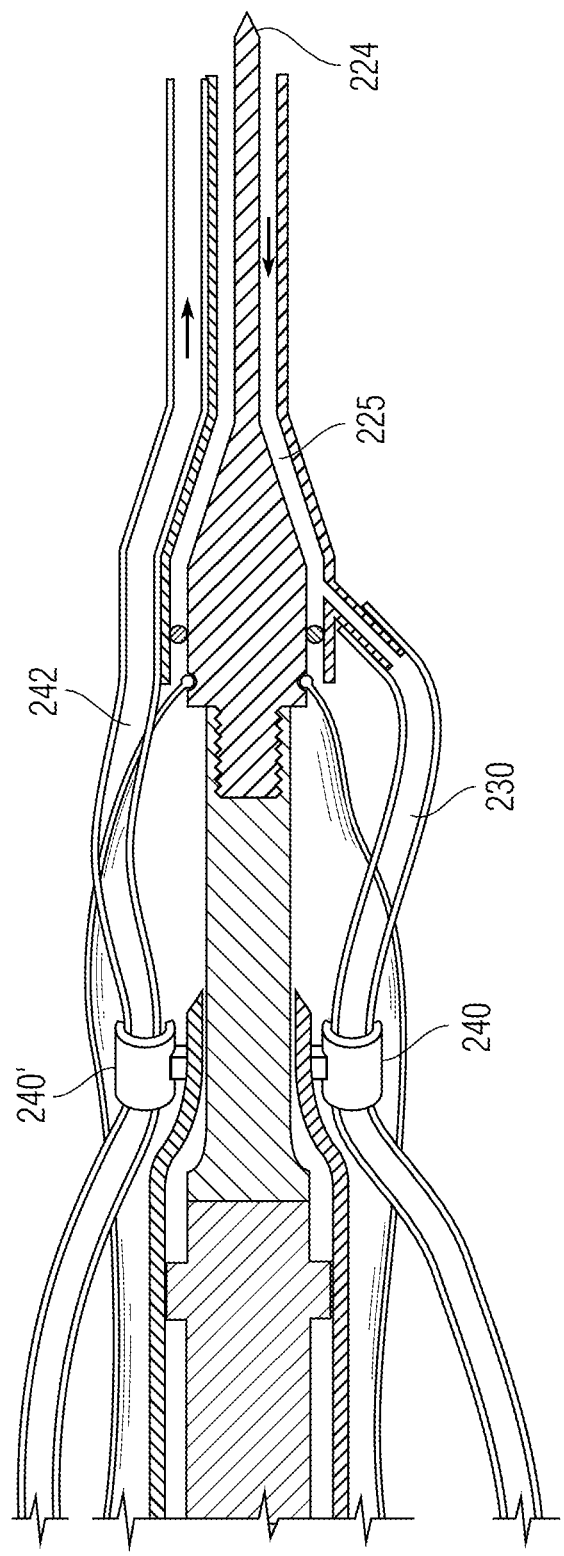
FIG. 4 is an embodiment of the present invention with the addition of an irrigation tube.

The structure shown in FIG. 3C has a single aspiration tube 230. In this case a second tube or instrument (not shown) would supply the irrigation fluid. However, as shown in FIG. 4 an additional tube 242 can be provided to preferably provide irrigation. Thus, in operation irrigation fluid is supplied to the surgical site where the vibrating knife 224 is emulsifying tissue. This tissue is removed from the site through aspiration channel 225. If desired, either during phacoemulsification or subsequent cleanup, the roles of channel 225 and tube 242 can be reversed. The openings of these tubes can have different shapes according to the procedure they are used for. In addition, the suction (aspiration) and irrigation force can be varied depending on the task. Also, for example during clean up, the ultrasonic vibration can be reduced or even halted.

The irrigation tube 242, like the aspiration tube 230, can be clipped into tube holders 240, 240' respectively to support them without violating the sterile region on the distal side of the bag or sheath 232.

Figure 5A:
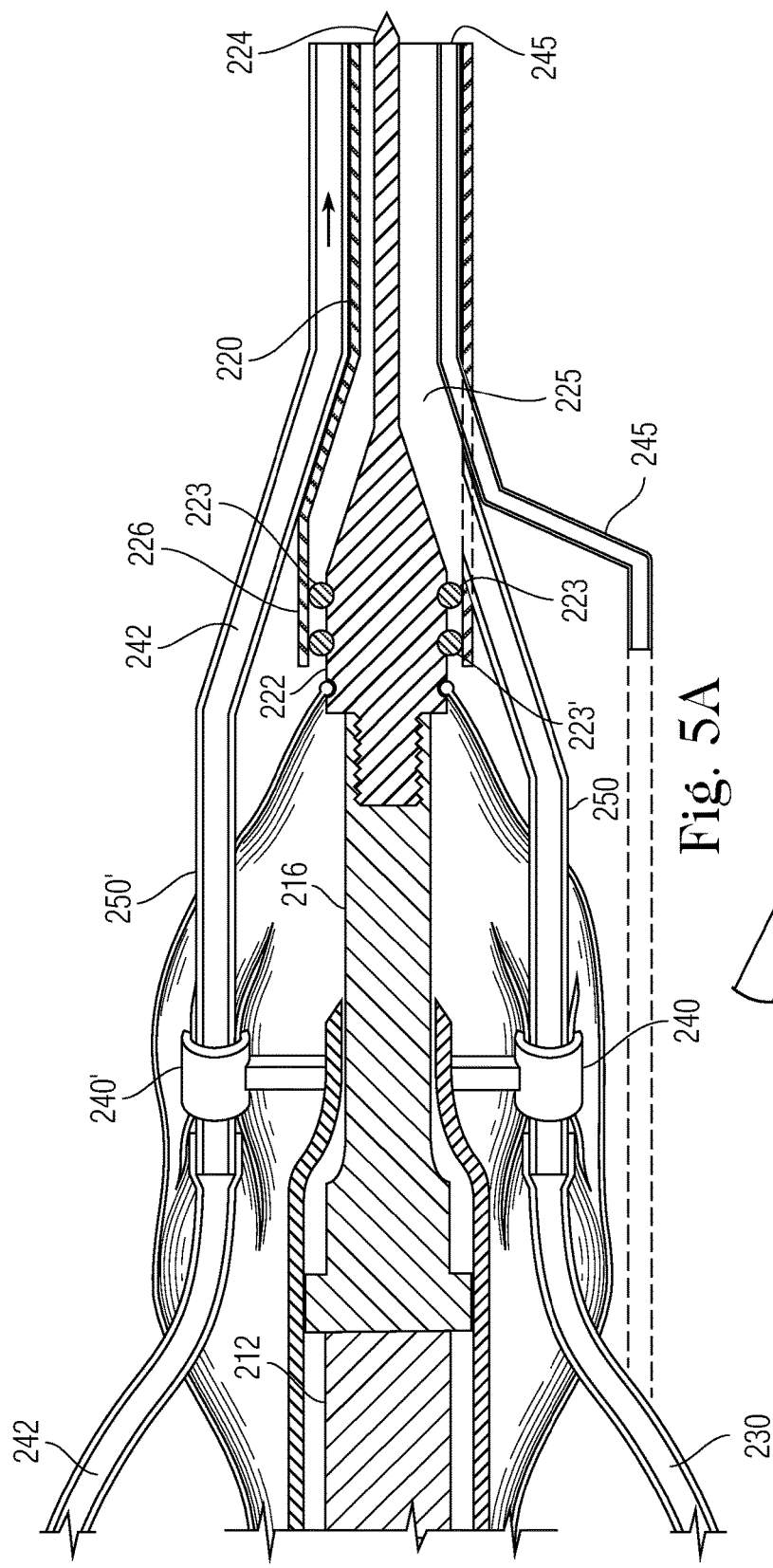
FIG. 5A is a second embodiment of the present invention in which an aspiration tube is included within the sleeve to allow for clean up after cataract surgery.

A second embodiment of the present invention is shown in FIG. 5A. As with the other embodiment it has a vibration transducer 212 attached to a connecting body 216. A hub 222 of a work tip with a knife 224 at its end is threaded into the connecting body 216. A sleeve 226 surrounds the hub and knife. The embodiment of FIG. 5A differs from the other embodiment in FIGS. 3 and 4 in that a third or extra tube 245 is provided within the sleeve 226. This tube 245 has a relatively small lumen and is used for aspiration during clean up.

The second embodiment also differs from the first in that irrigation tube 242 has a distal portion 250' that is rigid with a straight part that fits in tube holder 240' and then slopes downward to travel over the hub 222 and along the sleeve 226. Also, the aspiration tube 230 has a similar rigid portion 250 that can be held by tube holder 240, travels straight and then slopes down to enter into the rear end of sleeve 226. O-rings 223, 223' block off the end of channel 225. Tube 250 penetrates sleeve 226 and merges with channel 225. Tube 245 penetrates sleeve 226 at a different location distal of the O-ring 223 and continues as a tube in channel 225. Both tubes are in sealing engagement with the sleeve.

Figure 5B:
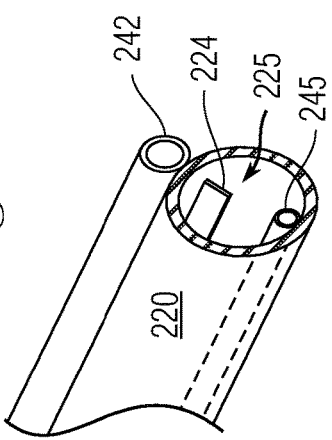
FIG. 5B is an enlarged perspective view of the end of the work tip of FIG. 5A.

As shown in FIG. 5A the hand piece is set up for phacoemulsification. The knife is vibrated at an ultrasonic frequency to emulsify the cataract tissue. At the same time irrigation fluid is supplied to the surgical site through tube 242 by means of part 250' As best seen in FIG. 5B, tissue pieces are aspirated into channel 225 at its distal end. This tissue may also be aspirated into tube 245 within the sleeve if the end of the tube is connected to an aspiration source (connecting line shown in dotted line in FIG. 5A). Because of the small size of tube 245, there may be no need to make this connection during a typical phacoemulsification operation.

Figure 6:
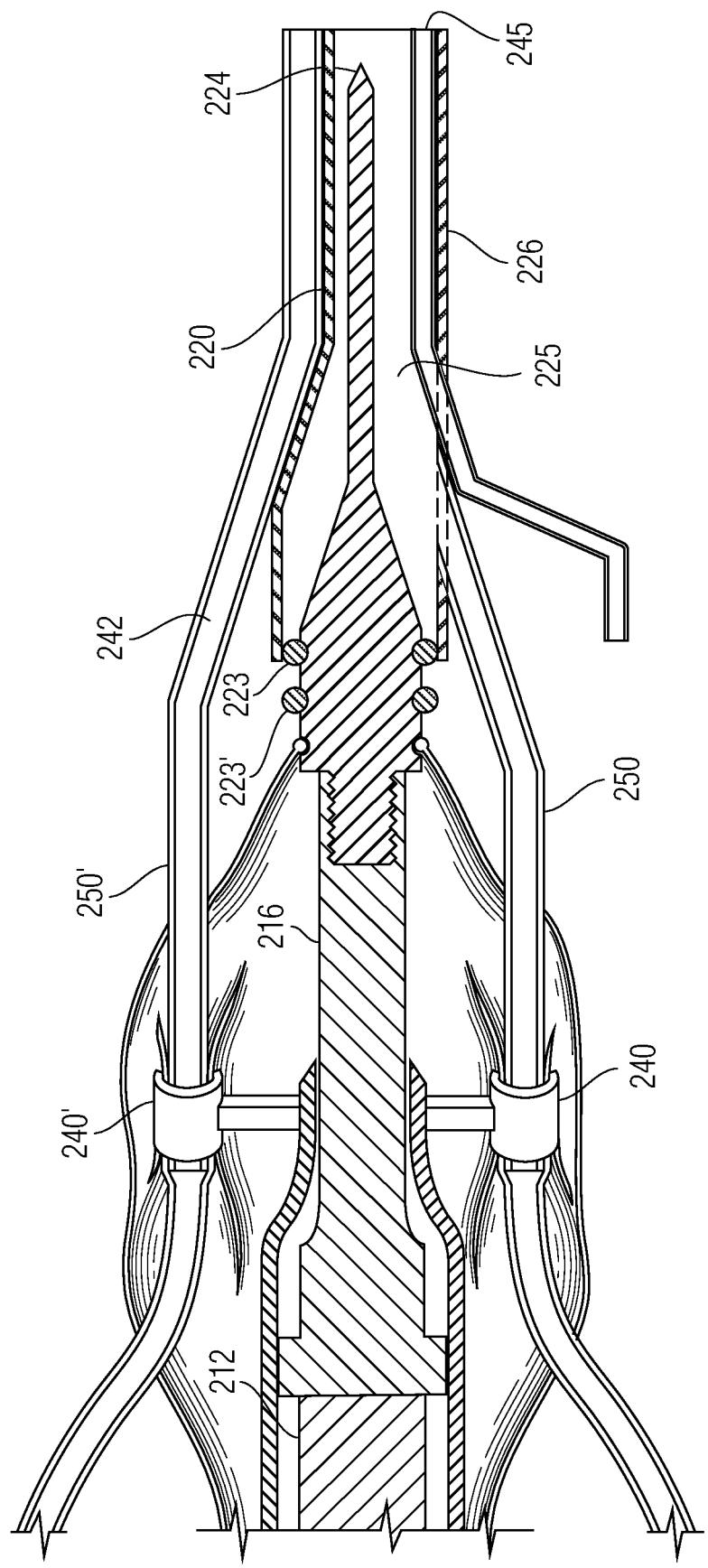
FIG. 6 shows the embodiment of FIG. 5A where the sleeve has been extended to cover the knife during a cleanup procedure.

Once the phacoemulsification operation is completed, typically the cleanup procedure is begun in order to remove remaining pieces of cataract tissue. With the second embodiment this can be achieved with the same tool and without removing the tool from the eye. As can be seen by comparing FIG. 5A to FIG. 6, the vibration force can be turned off and the surgeon can push the rigid parts 250, 250' through the tube holders 240, 240' toward the distal end. As a result the sleeve 226 covers the now stationary knife 224 so it will not harm the delicate tissue during cleanup. The flow of irrigation fluid would typically be slowed and the aspiration flow through channel 225 is stopped. However, O-ring 223' still blocks the proximal end of channel 225. During clean up the aspiration is only through much smaller tube 245.

Figure 2:
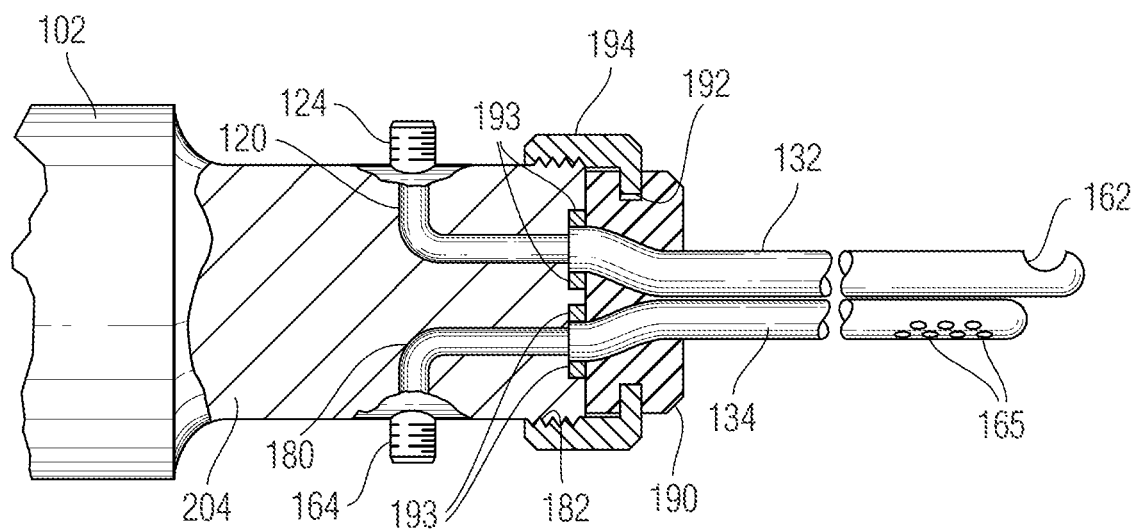
FIG. 2. is cross-sectional view of a prior art dual lumen surgical hand piece.

The distal ends of channel 225 and aspiration tube 245 are shown merely cut off. However, they can be shaped like the openings 162, 165 in FIG. 2 so as to have closed rounded ends or a plurality of small openings that allow the fluids to contact the tissue.

While the invention has been shown and described in connection with the removal of a cataract from the eye of a patient and subsequent I/A clean up, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. A surgical hand piece comprising:
a solid knife connected to a source of ultrasonic energy, said solid knife having a rectangular structure that tapers down to a cutting edge at its distal end;
a sleeve in which the solid knife is located;
a support for holding the sleeve with respect to the solid knife and damping a transfer of vibration of the solid knife into the sleeve;
a housing in which the source of ultrasonic energy is supported;
an aspiration tube connected to a fluid channel;
an irrigation tube located along the sleeve and extending to a region of a tip of the sleeve;
a tube holder attached to the housing said aspiration tube being located in the tube holder
a second tube holder attached to the housing, said irrigation tube being located in the second tube holder; and
wherein the aspiration tube and the irrigation tube have rigid parts extending from their distal ends so as to pass through the tube holders, wherein the rigid parts of the aspiration tube and irrigation tube are fastened to the sleeve and sliding the aspiration and irrigation tubes toward a distal end of the surgical hand piece causes the sleeve to extend over the solid knife.

2. The surgical hand piece according to claim 1 further including a connecting body and wherein the source of ultrasonic energy is an ultrasonic transducer attached to the connecting body.

3. The surgical hand piece according to claim 2 wherein the solid knife further includes a hub, said hub being detachably connected to the connecting body and having the solid knife connected to a distal end of the hub.

4. The surgical hand piece of claim 3 wherein said housing is connected to the connecting body at least in part at a null point in vibration of the connecting body.

5. The surgical hand piece of claim 4 further including a surgical bag connected to the hub and surrounding the housing.

6. The surgical hand piece of claim 5 wherein the surgical bag is located between said aspiration tube and the tube holder.

7. The surgical hand piece of claim 6 wherein the surgical bag is located between said irrigation tube and the second tube holder.

8. The surgical hand piece of claim 7 further including a small aspiration tube located in the sleeve and extending from a distal end of the small aspiration tube to a location near a proximal end of the small aspiration tube where the small aspiration tube passes through the sleeve, said small aspiration tube having a connection by which an aspiration source can be connected to the small aspiration tube.

9. The surgical hand piece of claim 1 wherein the support is a set of 0-rings.

10. The surgical hand piece of claim 1 wherein a space between the solid knife and sleeve forms a fluid channel, wherein the fluid channel is for one of providing irrigation fluid to a surgical site and aspirating fluid and tissue from the surgical site.

11. The surgical hand piece of claim 1 wherein the distal ends of the aspiration and irrigation tubes have different types and shapes of openings.

12. The surgical hand piece according to claim 1 wherein the solid knife has an enlarged hub at a proximal end of the solid knife and further including a flexible bag attached to the enlarged hub and surrounding the housing.

13. The surgical hand piece according to claim 12 wherein the flexible bag, solid knife and sleeve are sterile.

14. The surgical hand piece according to claim 12 wherein the flexible bag, solid knife and sleeve form a single use disposable unit.

* * * * *